(12) United States Patent
Wang

(10) Patent No.: US 7,394,075 B1
(45) Date of Patent: Jul. 1, 2008

(54) PREPARATION OF INTEGRATED CIRCUIT DEVICE SAMPLES FOR OBSERVATION AND ANALYSIS

(75) Inventor: Naiyi Wang, Fremont, CA (US)

(73) Assignee: Cypress Semiconductor Corporation, San Jose, CA (US)

( * ) Notice: Subject to any disclaimer, the term of this patent is extended or adjusted under 35 U.S.C. 154(b) by 206 days.

(21) Appl. No.: 11/352,437

(22) Filed: Feb. 9, 2006

Related U.S. Application Data

(60) Provisional application No. 60/654,388, filed on Feb. 18, 2005.

(51) Int. Cl.
*H01J 37/20* (2006.01)
(52) U.S. Cl. .................. 250/440.11; 250/304; 250/307; 250/311
(58) Field of Classification Search ............ 250/440.11, 250/304, 307, 311
See application file for complete search history.

(56) References Cited

U.S. PATENT DOCUMENTS

| | | | |
|---|---|---|---|
| 5,892,225 A * | 4/1999 | Okihara | 250/311 |
| 7,038,218 B2 * | 5/2006 | Lee et al. | 250/440.11 |
| 7,297,950 B2 * | 11/2007 | Lee et al. | 250/311 |
| 7,297,965 B2 * | 11/2007 | Kidron et al. | 250/492.2 |
| 2007/0158566 A1 * | 7/2007 | Ikeda | 250/311 |

OTHER PUBLICATIONS

Kevin McLlwrath & Nathan Wang, "A Novel FIB method to prepare TEM samples for 3D observation" Nov. 2004, pp. 320-323, Proceedings from the 30th International Symposium for Testing and Failure Analysis, California, U.S.A.

Jon C. Lee, David Su, & J.H. Chuang, "A Novel Application of the FIB Lift-out Technique for 3-D TEM Analysis", 2001, pp. 1551-1556, Microelectronics Reliability 41, Hsin-Chu, Taiwan.

Focused Ion Beam (FIB) Sample Prep—Welcome to Ceriumlabs; Webpage [online] [retrieved on Jan. 16, 2006]; Retrieved from the internet : http://www.ceriumlabs.com/services/analytical_imaging/FIB_dir.

N. Wang, J. Wu, & S. Daniel, "Grafting FIB "Lift-out" TEM Sample for Further Ion Milling and its application for semiconductor devices", Nov. 17, 2004, 2 pages; 30th International Symposium for Testing and Failure http://asm.confex.com/asm/istfa04/techprogram/paper_3138.htm.

Lucille A. Giannuzzi, et al., "FIB Lift-Out for Defect Analysis", 7 pages; Webpage [online] [retrieved on Jan. 16, 2006]; Retrieved from the internet: http://www.nanospective.com/publications/FIB%20Lift-Out%20for%20Defect%20Analysis.pdf.

Nanotechnology at Zyvex; Webpage [online] [retrieved on Jan. 17, 2006], 22 pages; Retrieved from the internet: <URL:http://www.zyvex.com/Products/TEMS_001a.htm.

* cited by examiner

*Primary Examiner*—Nikita Wells
*Assistant Examiner*—Johnnie L Smith, II
(74) *Attorney, Agent, or Firm*—Okamoto & Benedicto LLP

(57) ABSTRACT

In one embodiment, a sample of an integrated circuit device is prepared for observation in a transmission electron microscope (TEM). The sample may be placed on a surface formed by vertical edges of several TEM grids. The sample may be affixed to a vertical edge of one of the TEM grids. The TEM grid supporting the sample may be separated from the other TEM grids, and then placed in the TEM so that the sample may be observed.

20 Claims, 7 Drawing Sheets

PREPARATION OF INTEGRATED CIRCUIT DEVICE SAMPLES FOR OBSERVATION AND ANALYSIS

CROSS-REFERENCE TO RELATED APPLICATION

This application claims the benefit of U.S. Provisional Application No. 60/654,388, filed on Feb. 18, 2005, which is incorporated herein by reference in its entirety.

BACKGROUND OF THE INVENTION

1. Field of the Invention

The present invention relates generally to integrated circuit fabrication, and more particularly but not exclusively to techniques for preparing samples for transmission electron microscope (TEM) analysis.

2. Description of the Background Art

Fabrication of an integrated circuit device often includes analyzing topographies at different stages of the manufacturing process to insure that the device meets specified functionality requirements. By topographies it is meant a substrate or wafer, such as a semiconductor wafer, having one or more layers formed thereon, regardless of whether a functioning device has been formed from the topography or not.

A number of different techniques may be used to analyze device topography. For example, a cross-sectional analysis of the device topography may be performed using a transmission electron microscope (TEM). Generally, a TEM directs an electron beam at a prepared cross-sectional sample of the device while a photograph is simultaneously taken. Both the photograph and electron beam are used to analyze the exposed layers.

There are several different techniques or approaches for preparing cross-sectional samples of a device for TEM observation and analysis.

In mechanical polishing, the sample is sandwiched between a glass slide and silicon, and then polished using a traditional wedge polish technique.

The focused ion beam (FIB) in-situ lift-out (INLO) method takes advantage of an FIB instrument's deposition and cutting capability to attach or detach the sample to either a probe or a grid. A specialized probe in the FIB instrument's chamber is employed to move the sample around. After the sample is transferred from an original grid to a vertical grid, the FIB instrument is used to cut the sample to form a thin area for TEM observation. Systems for preparing and manipulating TEM samples by the FIB INLO method are commercially available from Omniprobe, Inc. of Dallas, Tex. Further details of the FIB INLO method are described in, for example, T. Yaguchi, Microscopy and Microanalysis, Vol. 7, No. Supp/2, p. 938, 2001, and in K. McIlwrath and N. Wang, ISTFA 2004, p. 320.

In the Glue+LO (lift-out) method, the sample is glued to silicon with conductive glue and, after the glue has cured, the FIB instrument is used to prepare the sample using a traditional lift-out technique. Typically, the sample is lifted out using glass needle. Further details of this method are described in, for example, Jon C. Lee, Microelectronics Reliability 41 (2001) 1551-1556.

Heretofore, the above approaches have not proven wholly satisfactory for a number of reasons. In particular, sample handling in the mechanical polishing method is extremely difficult and is highly dependent on the skill of the person doing the work. The FIB INLO method requires a focused ion beam (FIB) instrument with specialized probe attachments. Moreover, constant exposure to an ion beam may cause crystal structure damage to the sample, leading to erroneous analysis. Similarly, the Glue+LO method can cause sample crystal structure damage and sample loss during the lift-out. Furthermore, the particles in the glue can cause a non-uniform sample thickness, further complicating the analysis. Accordingly, there is a need for an improved technique of preparing and manipulating samples for TEM observation and analysis.

SUMMARY

In one embodiment, a sample of an integrated circuit device is prepared for observation in a transmission electron microscope (TEM). The sample may be placed on a surface formed by vertical edges of several TEM grids. The sample may be affixed to a vertical edge of one of the TEM grids. The TEM grid supporting the sample may be separated from the other TEM grids, and then placed in the TEM so that the sample may be observed.

These and other features of the present invention will be readily apparent to persons of ordinary skill in the art upon reading the entirety of this disclosure, which includes the accompanying drawings and claims.

The use of the same reference label in different drawings indicates the same or like components.

DETAILED DESCRIPTION

In the present disclosure, numerous specific details are provided, such as examples of apparatus, components, and methods, to provide a thorough understanding of embodiments of the invention. Persons of ordinary skill in the art will recognize, however, that the invention can be practiced without one or more of the specific details. In other instances, well-known details are not shown or described to avoid obscuring aspects of the invention.

The present invention is described in the context of preparing and manipulating samples of an integrated circuit device for transmission electron microscope (TEM) observation and analysis in three dimensions. It is to be understood, however, that the invention may be also be employed to prepare and manipulate samples for use with observation and analysis apparatus other than a TEM.

FIGS. 1-7 pictorially illustrate a method of preparing and manipulating a TEM sample in accordance with an embodiment of the present invention. Each of FIGS. 1-7 constitutes a step in the method.

Figure 1:
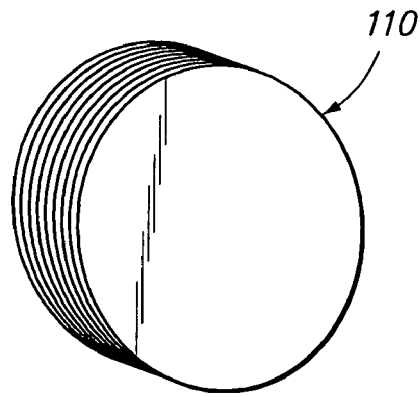
FIGS. 1-4, 5A, 5B, 5C, 6A, 6B, 6C, 7A, and 7B pictorially illustrate a method of preparing and manipulating a TEM sample in accordance with an embodiment of the present invention.

In FIG. 1, multiple TEM grids 110 are gathered to form a group of grids. Each TEM grid 110 may be punched out of a sheet of metal, for example. In one embodiment, each TEM grid 110 comprises a metal disc, such as a copper disc having a diameter of 3 mm and a thickness of 1 mm. In that example, each TEM grid 110 is punched out of a 1 mm thick copper sheet metal. The number and dimensions of TEM grids 110 in the group of grids depends on the particulars of the application.

Figure 2:
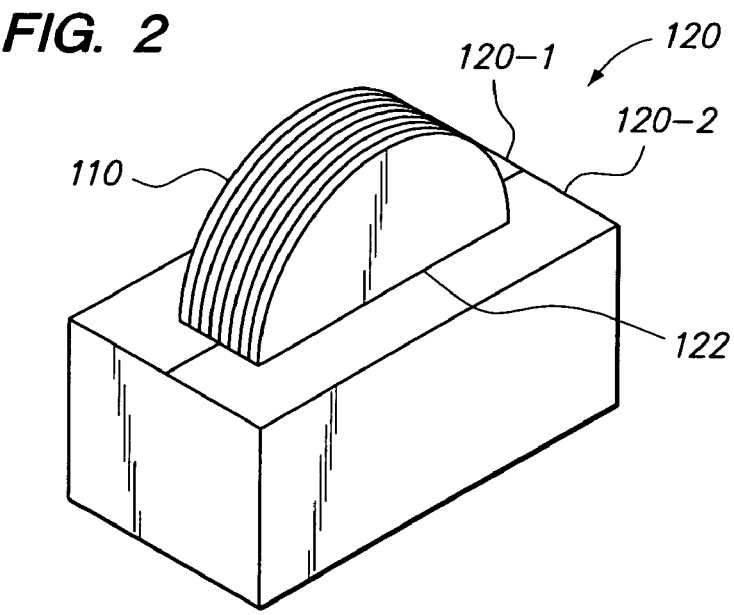

In FIG. 2, the TEM grids 110 are vertically mounted in a slot 122 of a stub 120 such that the edges of the TEM grids 110 stick out of the stub 120 for subsequent polishing. The stub 120 facilitates polishing of the TEM grids 110 to form a flat surface on which the sample may be transferred. In one embodiment, the stub 120 is a two-piece stub comprising a stub portion 120-1 and a stub portion 120-2. The stub portions 120-1 and 120-2 may be joined together by any suitable removable fastener (not shown). The stub portions 120-1 and 120-2 may be separated to facilitate removal of the TEM grids 110 from the stub after the sample has been prepared.

Figure 3:
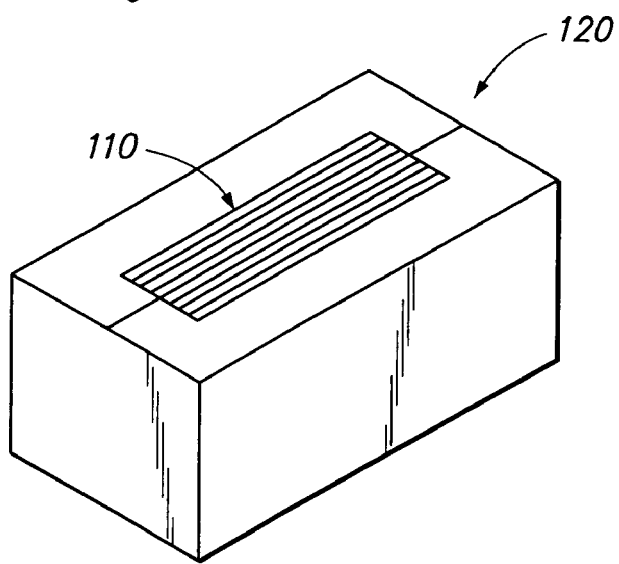

In FIG. 3, vertical edges of the TEM grids 110 are polished in the stub 120 to provide a relatively large flat surface on which the sample may be transferred. In one embodiment, portions of the TEM grids 110 exposed above the stub 120 are polished off to form a flat surface with the top surface of the stub 120. That is, the stub 120 provides a polishing stop. The edges of the TEM grids 110 may be polished using a variable speed polishing wheel commonly used in the semiconductor industry, for example.

As will be more apparent below, the relatively flat surface formed by the polished TEM grids 110 facilitates transfer of the sample to the vertical edges of the TEM grids 110. The polished edges also facilitate adhesion of a sample that is mounted on a mesh with carbon film. After the sample is transferred to an edge of one of the TEM grids 110, that TEM grid 110 may then be separated from the rest of the TEM grids 110 (see FIG. 7) for observation and analysis in a TEM.

Figure 4:
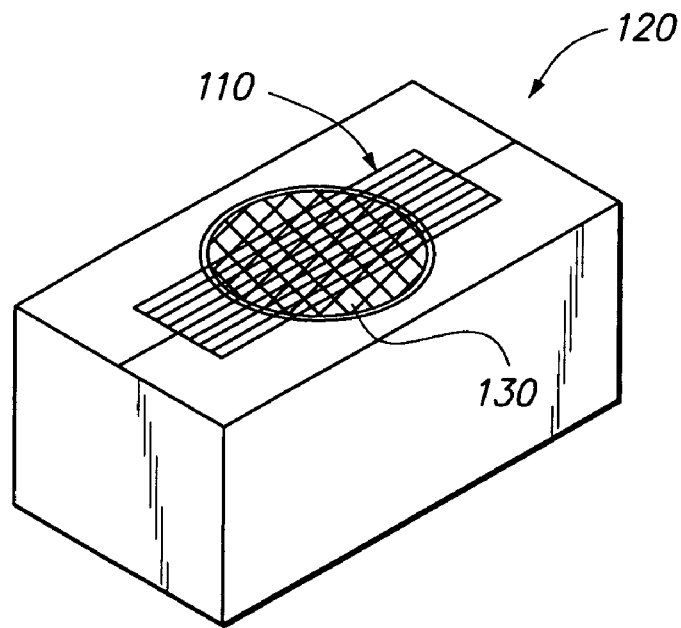

In FIG. 4, the sample is laid on the polished edges of the TEM grids 110. In one embodiment, the sample comprises a portion of an integrated circuit device obtained using a conventional lift-out (LO) technique, such as FIB INLO techniques. For example, an FIB instrument's milling, etching, and welding capabilities may be used to lift out the portion of interest from the integrated circuit device. The sample may be mounted or held in a mesh by a carbon film. Obtaining samples of integrated circuit devices by lift-out, in general, is known in the art and not further described here.

Figure 5A:
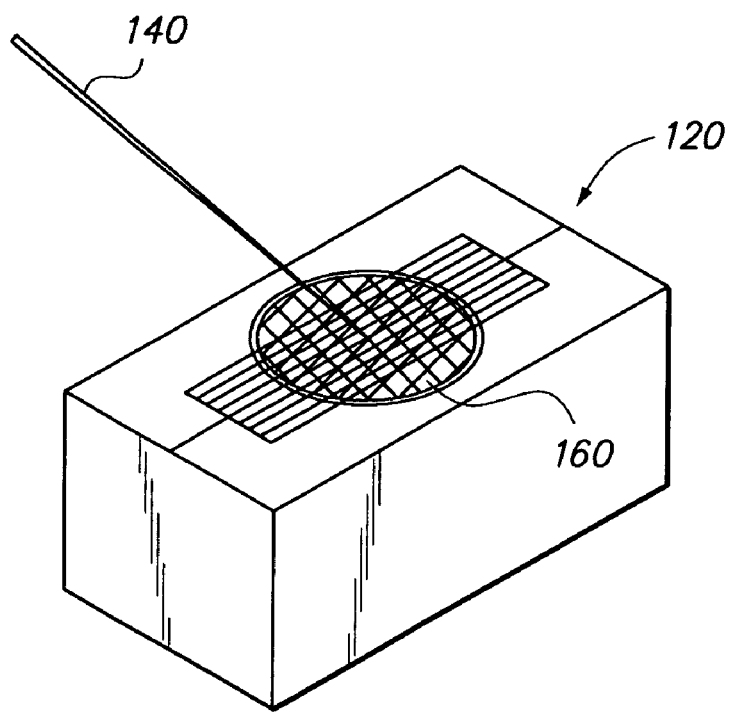
Figure 5B:
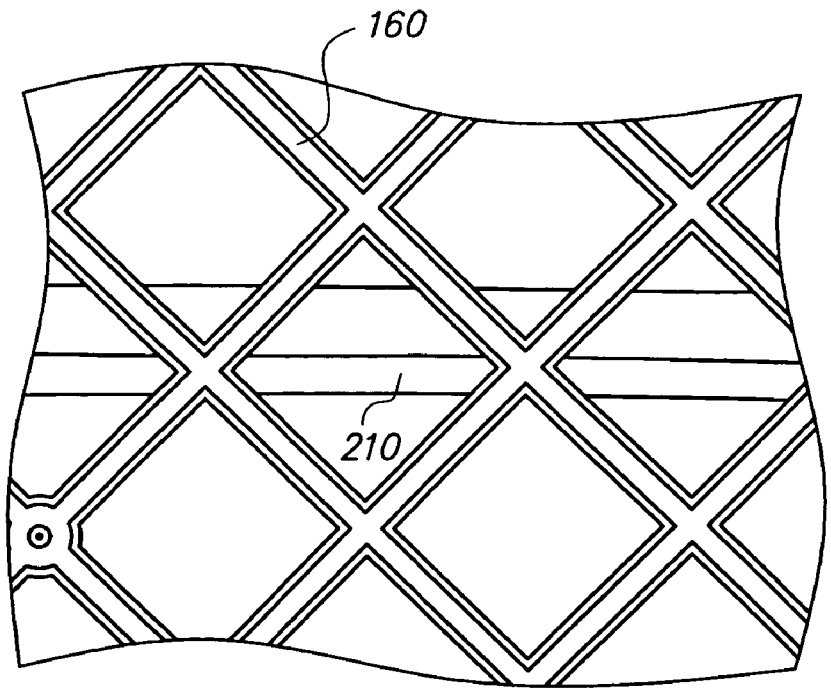
Figure 5C:
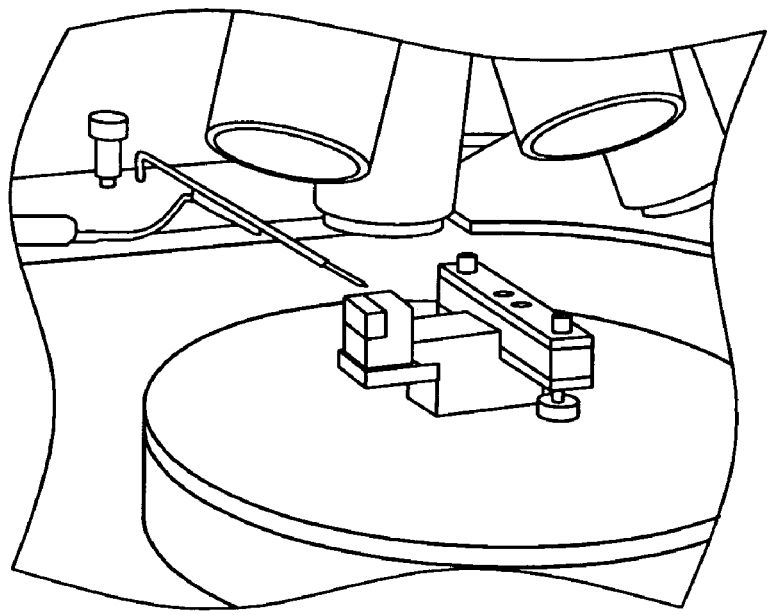

In FIG. 5, which consists of FIGS. 5A, 5B, and 5C, the sample is attached to one of the TEM grids 110. Referring to FIG. 5A, a manipulator 140 may be used to push or manipulate the sample on the mesh 160 to make the sample stick to an edge of one of the TEM grids 110. The carbon film on the sample sticks to the polished edges of the TEM grids 110. The manipulator 140 may be used to push the carbon film down and to break the sample free from the mesh 160. The manipulator 140 may comprise a glass needle, for example. The mesh 160 is removed once the sample is attached to an edge of one of the TEM grids 110. FIG. 5B shows a photograph of a TEM sample 210 mounted on a mesh 160. FIG. 5C shows a photograph of a manipulator/microscope setup for attaching the sample 210 to an edge of a single TEM grid 110.

Figure 6A:
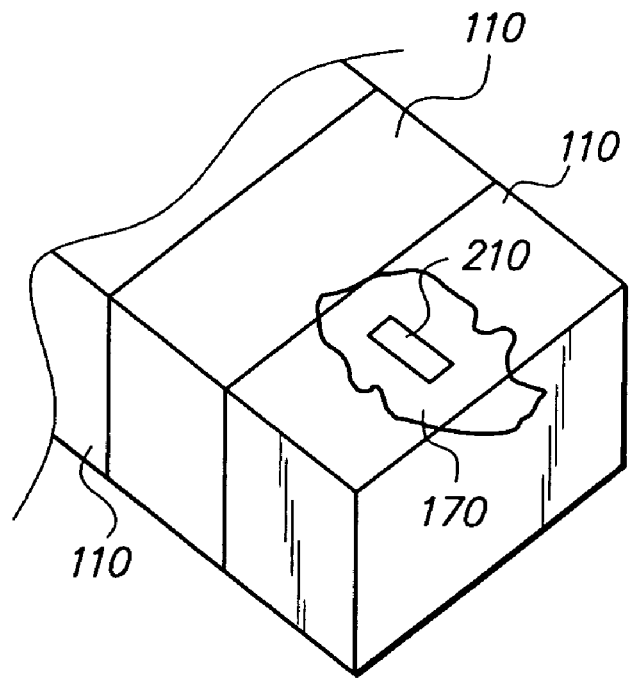
Figure 6B:
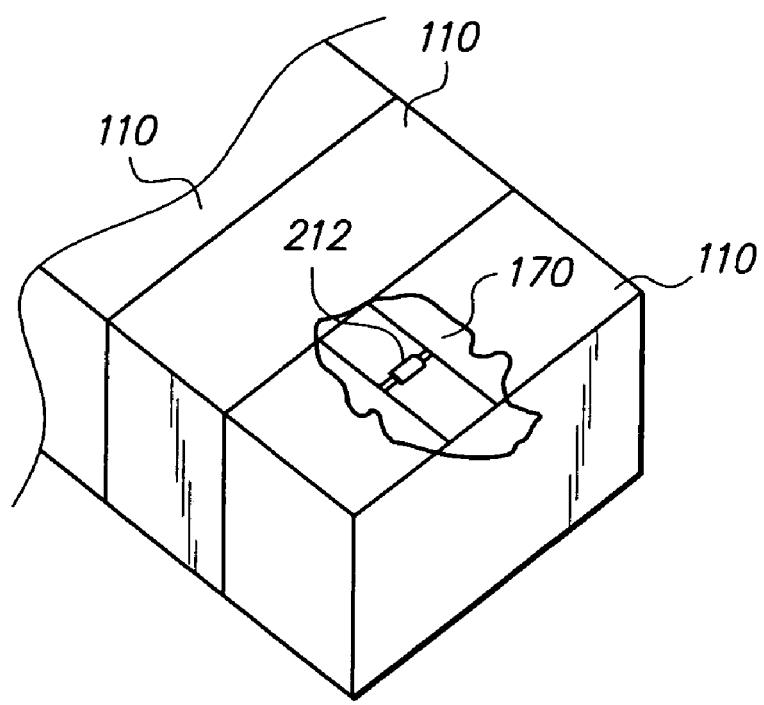
Figure 6C:
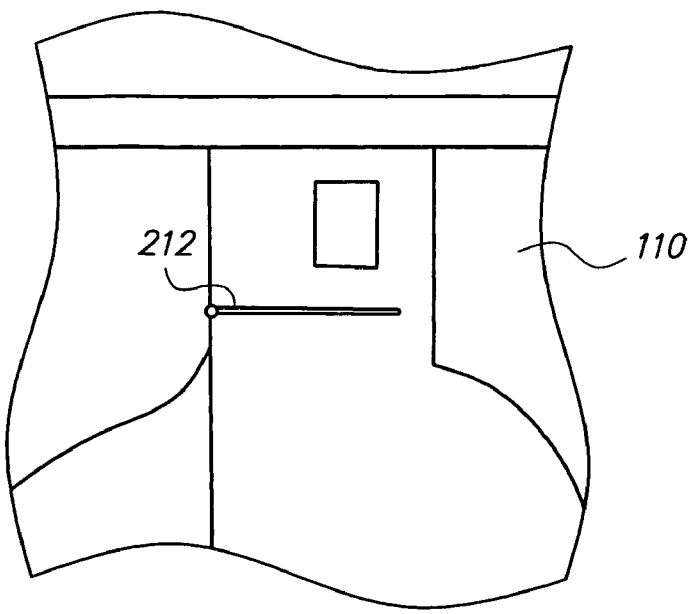

In FIG. 6, which consists of FIGS. 6A, 6B, and 6C, a vertical thin film is cut from the sample. FIG. 6A shows the sample 210 on a polished vertical edge of single TEM grid 110 after the mesh 160 is removed. FIG. 6A also shows the remaining carbon film 170 from the mesh 160. Note that the carbon film 170 may span more than one TEM grid 160. As can be appreciated, using several TEM grids 110 and polishing them together allows their edges to form a relatively large flat surface that facilitates transfer of the sample 210 from the mesh 160 to an edge of a single TEM grid 110. FIG. 6B shows a vertical thin film final sample 212 cut from the sample 210. In one embodiment, the final sample 212 is cut from the sample 210 using an FIB instrument. The final sample 212 may be in the order of 0.1 µm, for example. FIG. 6C shows a TEM photograph of an example final sample 212 on a vertical edge of a TEM grid 110.

Figure 7A:
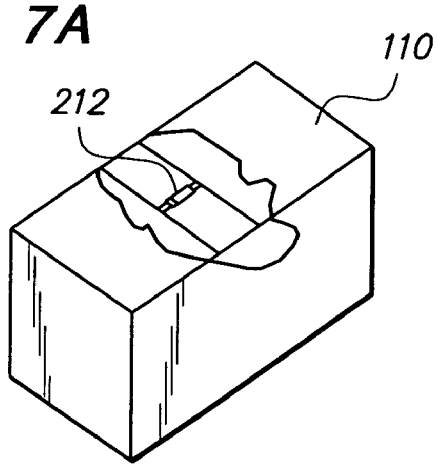
Figure 7B:
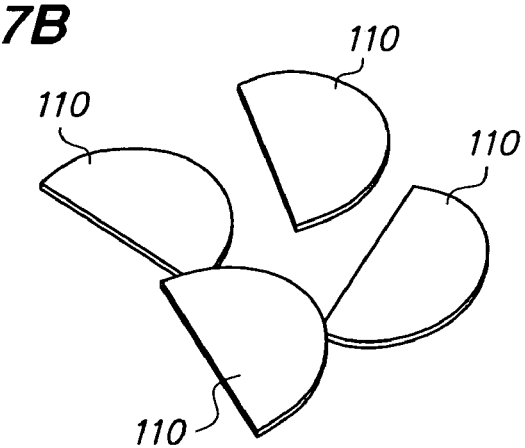

In FIG. 7, which consists of FIGS. 7A and 7B, the TEM grid 110 on which the final sample 212 is attached is separated from the other TEM grids 110. In one embodiment, the TEM grids 110 are separated by separating the portions 120-1 and 120-2 of the stub 120. FIG. 7A shows the separated TEM grid 110 containing the final sample on its vertical edge. FIG. 7B shows a photograph of several separated TEM grids 110. The separated TEM grid 110 containing the final sample 212 may then be placed in the TEM to support the final sample while being observed using the TEM. For example, electron beams of the TEM may be passed through the final sample 212 while being supported by the TEM grid 110.

As can be appreciated, the above-described method for preparing and manipulating a TEM sample minimizes the use of FIB instruments to prevent damaging the sample. For example, the method may employ FIB instruments to get a sample from an integrated circuit device (e.g., for lift-out) and to cut the final sample. The remaining steps may involve relatively simple manipulations by an operator. A specialized FIB probe is also not required because manipulation of the sample on the vertical edges of the TEM grids 110 may be performed by the operator using a glass needle, for example. The simplicity of the method allows it be performed relatively fast (reducing turn-around time), with a relatively high success rate, and without the need for specialized probes.

Figure 8A:
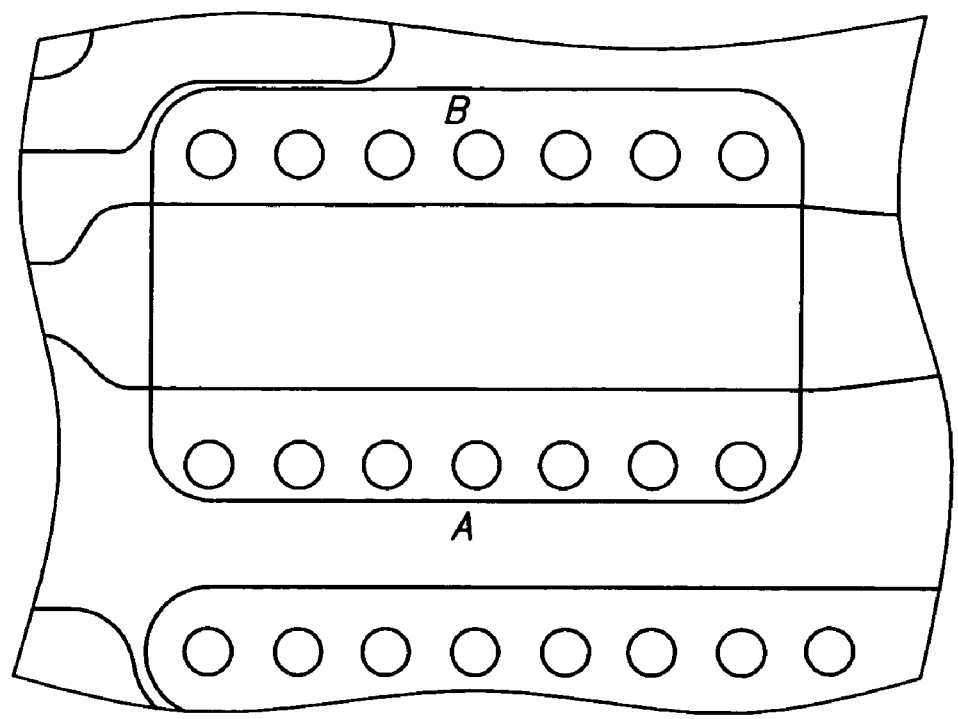
FIGS. 8A, 8B, 9A, and 9B show photographs of exemplary samples prepared and manipulated for TEM analysis in accordance with an embodiment of the present invention.
Figure 8B:
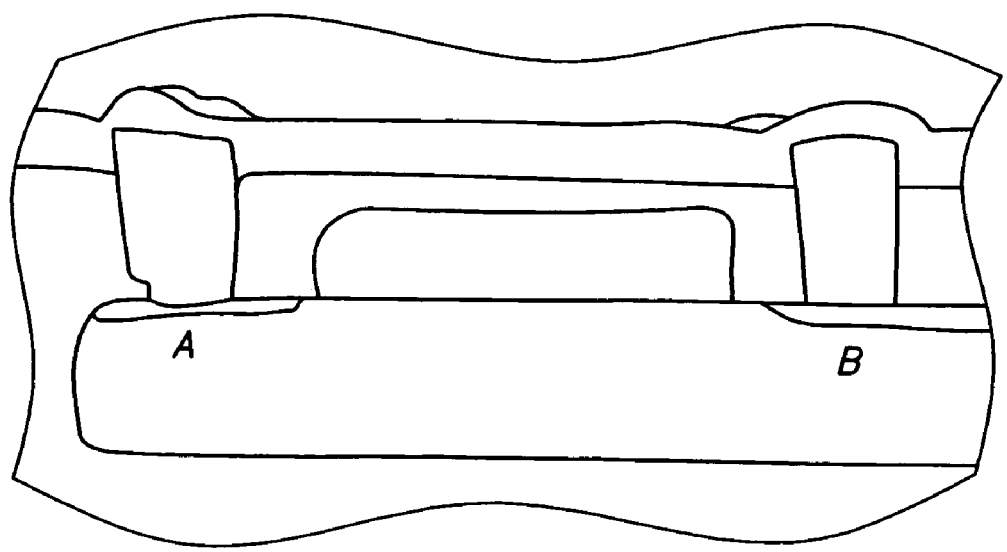
Figure 9A:
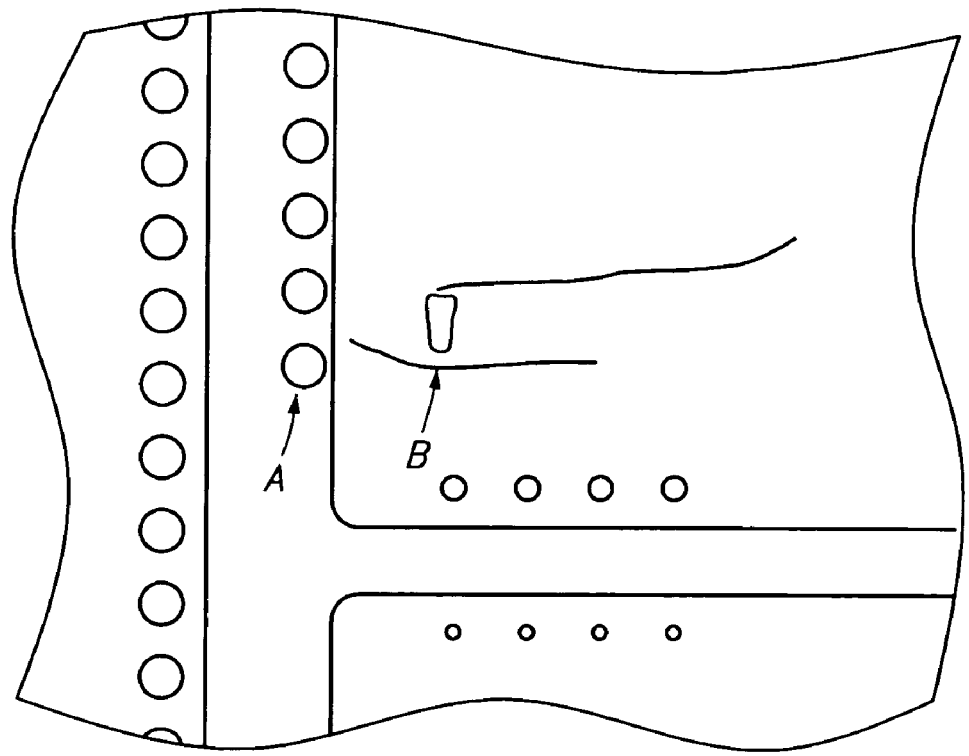
Figure 9B:
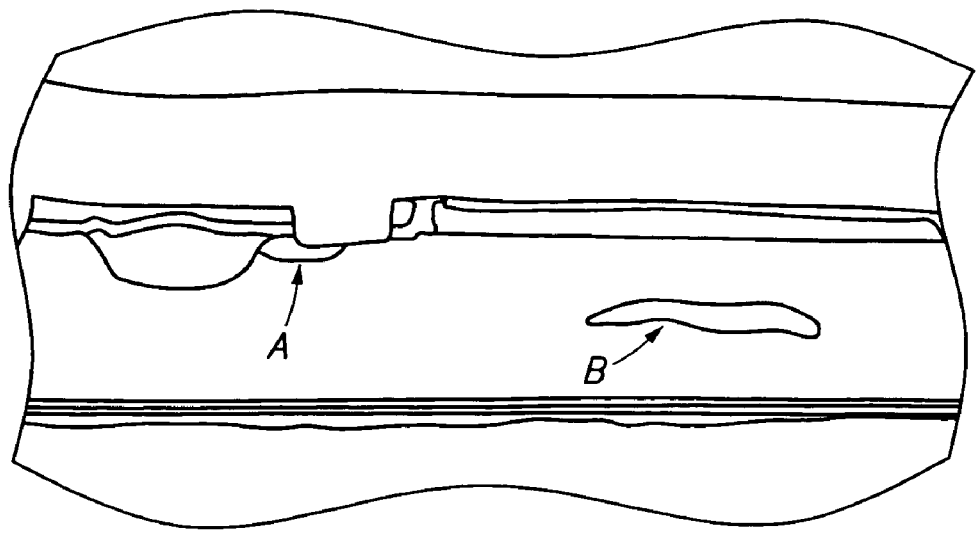

FIGS. 8 and 9 show TEM photographs of exemplary samples prepared and manipulated for TEM analysis in accordance with an embodiment of the present invention. FIG. 8A shows a plane view of an integrated circuit device topography, while FIG. 8B shows a cross-section of the same topography. Likewise, FIG. 9A shows a plane view of another integrated device topography, while FIG. 9B shows a cross-section of the same topography. The TEM photographs have been labeled with points "A" and "B" for reference purposes. The capability to take TEM photographs of different views of the sample allows for three-dimensional analysis of the sample.

Improved techniques for preparing and manipulating a sample for TEM observation and analysis have been disclosed. While specific embodiments of the present invention have been provided, it is to be understood that these embodiments are for illustration purposes and not limiting. Many additional embodiments will be apparent to persons of ordinary skill in the art reading this disclosure.

What is claimed is:

1. A method of preparing and manipulating a sample for use with a transmission electron microscope (TEM):

polishing vertical edges of a plurality of TEM grids to form a surface on which to place a sample of an integrated circuit device;

placing the sample on the surface;

transferring the sample to a vertical edge of a single TEM grid in the plurality of TEM grids;

separating the single TEM grid from the plurality of TEM grids;

placing the single TEM grid in the TEM; and observing the sample using the TEM.

2. The method of claim 1 wherein polishing the vertical edges of the plurality of TEM grids comprises:

grouping the plurality of TEM grids;

placing the TEM grids vertically in a stub; and polishing portions of the TEM grids exposed above the stub using the stub as a polishing stop.

3. The method of claim 1 wherein the sample is held on a mesh with a carbon film.

4. The method of claim 3 wherein transferring the sample to the vertical edge of the single TEM grid comprises:
   pushing the sample down to make the sample stick to the vertical edge of the single TEM grid; and
   removing the mesh from the sample.

5. The method of claim 4 wherein the sample is pushed down to the vertical edge of the single TEM grid using a glass needle.

6. The method of claim 1 wherein each TEM grid in the plurality of TEM grids comprises a metallic disc.

7. The method of claim 1 wherein each TEM grid in the plurality of TEM grids comprises copper.

8. The method of claim 1 wherein the sample comprises a portion of the integrated circuit device obtained using a focused ion beam (FIB) to lift out the portion from the integrated circuit device.

9. The method of claim 1 wherein separating the single TEM grid from the plurality of grids comprises:
   separating pieces of a stub holding the plurality of TEM grids.

10. The method of claim 1 further comprising:
    after transferring the sample to the vertical edge of the single TEM grid but before separating the single TEM grid from the plurality of TEM grids, cutting a thin film from the sample.

11. A method of preparing and manipulating a TEM sample, the method comprising:
    gathering a plurality TEM grids to form a group of TEM grids, each TEM grid in the plurality of TEM grids comprising a metallic disc;
    polishing edges of the plurality of TEM grids to form a flat surface;
    placing a mesh containing a sample of an integrated circuit device on the flat surface;
    pushing down the sample to an edge of a selected TEM grid in the plurality of TEM grids to make the sample stick to the selected TEM grid;
    removing the mesh from the flat surface while retaining the sample to the selected TEM grid;
    modifying the sample to form a vertical thin film while the sample is on the selected TEM grid;
    separating the selected TEM grid from the plurality of TEM grids; and
    using a TEM to observe the thin film.

12. The method of claim 11 wherein modifying the sample to form a vertical thin film is performed using a focused ion beam (FIB).

13. The method of claim 11 wherein the edges of the plurality of TEM grids are polished while the plurality of TEM grids are mounted vertically in a stub.

14. The method of claim 13 wherein portions of the plurality of TEM grids above the stub are removed to form the flat surface with a top surface of the stub.

15. The method of claim 11 wherein each TEM grid in the plurality of TEM grids is punched out from a sheet of metal comprising copper.

16. A method of preparing and manipulating a sample of an integrated circuit device for observation, the method comprising:
    removing a portion of an integrated circuit device to form a sample;
    placing the sample on a surface formed by edges of a plurality of grids;
    transferring the sample to an edge of a grid in the plurality of grids;
    separating the grid from the plurality of grids; and
    observing the sample using an observation instrument.

17. The method of claim 16 wherein the observation instrument comprises a TEM.

18. The method of claim 16 wherein the surface formed by the edges of the plurality of grids is formed by polishing edges of the plurality of grids.

19. The method of claim 18 wherein the plurality of grids comprise metallic discs.

20. The method of claim 19 further comprising:
    after transferring the sample to an edge of the grid but before separating the grid from the plurality of grids, cutting a thin film of the sample for observation using the observation instrument.

* * * * *